(12) United States Patent
Beller et al.

(10) Patent No.: US 7,371,909 B2
(45) Date of Patent: May 13, 2008

(54) METHOD FOR PRODUCING 1-OLEFINS USING PALLADIUM CARBENE COMPOUNDS

(75) Inventors: Matthias Beller, Nienhagen (DE); Ralf Jackstell, Cuxhaven (DE); Holger Klein, Rostock (DE); Dirk Roettger, Recklinghausen (DE); Klaus-Diether Wiese, Haltern (DE); Dietrich Maschmeyer, Recklinghausen (DE); Axel Tuchlenski, Muelheim (DE); Alfred Kaizik, Marl (DE); Silvia Santiago Fernandez, Oberhausen (DE)

(73) Assignee: Oxeno Olefinchemie GmbH, Marl (DE)

( * ) Notice: Subject to any disclaimer, the term of this patent is extended or adjusted under 35 U.S.C. 154(b) by 669 days.

(21) Appl. No.: 10/490,038

(22) PCT Filed: Oct. 1, 2002

(86) PCT No.: PCT/EP02/10971

§ 371 (c)(1),
(2), (4) Date: Mar. 19, 2004

(87) PCT Pub. No.: WO03/031379

PCT Pub. Date: Apr. 17, 2003

(65) Prior Publication Data
US 2004/0242947 A1    Dec. 2, 2004

(30) Foreign Application Priority Data
Oct. 6, 2001    (DE) ................................ 101 49 348

(51) Int. Cl.
C07C 4/02    (2006.01)
(52) U.S. Cl. ...................................... 585/329; 585/324
(58) Field of Classification Search ................ 585/329, 585/324
See application file for complete search history.

(56) References Cited

U.S. PATENT DOCUMENTS

| | | |
|---|---|---|
| 6,015,928 A | 1/2000 | Gubisch et al. |
| 6,184,424 B1 | 2/2001 | Bueschken et al. |
| 6,239,318 B1 | 5/2001 | Schuler et al. |
| 6,331,657 B1 | 12/2001 | Kaizik et al. |
| 6,403,836 B2 | 6/2002 | Kaizik et al. |
| 6,407,295 B1 | 6/2002 | Kaizik et al. |
| 6,433,230 B1 | 8/2002 | Bueschken et al. |
| 6,482,992 B2 | 11/2002 | Scholz et al. |
| 6,492,564 B1 | 12/2002 | Wiese et al. |
| 6,500,991 B2 | 12/2002 | Wiese et al. |
| 6,555,716 B2 | 4/2003 | Protzmann et al. |
| 6,570,033 B2 | 5/2003 | Rottger et al. |
| 6,603,047 B2 | 8/2003 | Wiese et al. |
| 6,627,782 B2 | 9/2003 | Kaizik et al. |
| 6,680,414 B2 | 1/2004 | Knoop et al. |
| 6,720,457 B2 | 4/2004 | Drees et al. |
| 6,818,770 B2 | 11/2004 | Selent et al. |
| 6,924,389 B2 | 8/2005 | Jackstell et al. |
| 6,956,133 B2 | 10/2005 | Jackstell et al. |
| 6,960,699 B2 | 11/2005 | Totsch et al. |
| 7,009,068 B2 | 3/2006 | Schmutzler et al. |
| 7,109,346 B2 | 9/2006 | Beller et al. |
| 2004/0059170 A1 | 3/2004 | Rottger et al. |
| 2004/0236133 A1 | 11/2004 | Selent et al. |
| 2004/0238787 A1 | 12/2004 | Wiese et al. |
| 2005/0038273 A1 | 2/2005 | Rottger et al. |
| 2005/0043279 A1 | 2/2005 | Selent et al. |
| 2005/0182277 A1 | 8/2005 | Totsch et al. |
| 2005/0209489 A1 | 9/2005 | Moller et al. |
| 2005/0234270 A1 | 10/2005 | Kaizik et al. |
| 2005/0256281 A1 | 11/2005 | Grund et al. |
| 2006/0128998 A1 | 6/2006 | Lueken et al. |
| 2006/0129004 A1 | 6/2006 | Lueken et al. |
| 2006/0161017 A1 | 7/2006 | Grass et al. |
| 2006/0183936 A1 | 8/2006 | Grass et al. |
| 2006/0241324 A1 | 10/2006 | Moeller et al. |

FOREIGN PATENT DOCUMENTS

| | | |
|---|---|---|
| DE | 10105751 | 8/2002 |
| EP | 0440995 | 6/1991 |
| WO | 9210450 | 6/1992 |

OTHER PUBLICATIONS

U.S. Appl. No. 10/562,454, filed Dec. 27, 2005, Krissmann et al.
U.S. Appl. No. 10/538,359, filed Jun. 13, 2005, Rottger et al.
U.S. Appl. No. 10/517,620, filed Dec. 23, 2004, Rottger et al.
U.S. Appl. No. 10/497,034, filed May 28, 2004, Beller et al.

*Primary Examiner*—Thuan Dinh Dang
(74) *Attorney, Agent, or Firm*—Oblon, Spivak, McClelland, Maier & Neustadt, P.C.

(57) ABSTRACT

The invention relates to a process 1-olefins by telomerization of compounds having conjugated double bonds with a telogen in the presence of a noble metal telomerization catalyst, hydrogenation of the telomer and cleavage of the hydrogenated intermediate. Use of the 1-olefin as comonomer.

24 Claims, No Drawings

METHOD FOR PRODUCING 1-OLEFINS USING PALLADIUM CARBENE COMPOUNDS

BACKGROUND OF THE INVENTION

1. Field of the Invention

The invention relates to a process for preparing 1-olefins by telomerization of compounds having conjugated double bonds with a telogen in the presence of a noble metal telomerization catalyst, hydrogenation of the telomer and cleavage of the hydrogenated intermediate.

2. Description of the Background

1-Olefins such as 1-octene are used in large quantities in the production of various chemical products. For example, surface-active substance, plasticizers, lubricants and polymers are produced from 1-octene. Another large application is its use as comonomer in polymers, in particular in polyethylene.

Virtually all processes used commercially at the present time for producing 1-octene are based on the raw material ethene. Ethene is oligomerized to give a product spectrum of α-olefins as main products. With appropriate choice of catalyst and process conditions, the amount of 1-octene in the product can be optimized and is then about 25%. Apart from these processes by means of which the major part of the 1-octene produced is obtained, the isolation of 1-octene from the product mixture from the Fischer-Tropsch reaction has attained some importance.

Apart from the ethene-based processes, processes which use 1,3-butadiene as raw material for preparing 1-octene are also known from the literature. However, 1-octene is not obtainable directly from butadiene, for example by means of dimerization, but is obtained after a plurality of process steps. Thus, the patent application WO 92/10450 describes a process in which 1,3-butadiene is reacted preferably with methanol or ethanol to form a 2,7-octadienyl ether which is then hydrogenated to the octyl ether and is then cleaved to give 1-octene. EP-A-0 440 995 follows an analogous route, but the reaction in the first step is with a carboxylic acid. The first process step, which is generally referred to as telomerization, is involved in both the processes. In telomerization, a telogen (in EP-A-0 440 995 the carboxylic acid) is generally reacted with a taxogen (1,3-butadiene, 2 equivalents) to form a telomer.

Examples of telomerization reactions are described, inter alia, in E. J. Smutny, J. Am. Chem. Soc. 1967, 89, 6793; S. Takahashi, T. Shibano, N. Hagihara, Tetrahedron Lett. 1967, 2451; EP-A-0 561 779, U.S. Pat. Nos. 3,499,042, 3,530,187, GB 1 178 812, NL 6 816 008, GB 1 248 593, U.S. Pat. Nos. 3,670,029, 3,670,032, 3,769,352, 3,887,627, GB 1 354 507, DE 20 40 708, U.S. Pat. Nos. 4,142,060, 4,146,738, 4,196, 135, GB 1, 535 718, U.S. Pat. No. 4,104,471, DE 21 61 750 and EP-A-0 218 100.

In the known processes for preparing 1-octene on the basis of butadiene, as described, for example, in WO 92/10450 or EP-A-0 440 995, the 1-octene is obtained by cleavage of an n-octane substituted in the 1 position. The selectivities in this step are often unsatisfactory. Thus, WO 92/10450 reports a selectivity to octenes of 66% at a conversion of 80% in the cleavage of 1-methoxyoctane.

Catalysts which have been found to be effective for telomerization are halogen-free palladium(0) and palladium (II) compounds (A. Behr, in "*Aspects of Homogeneous Catalysis*"; editor R. Ugo, D. Reidel Publishing Company, Doordrecht/Boston/Lancaster, 1984, Vol. 5, 3). In addition, compounds of other transition metals such as cobalt (R. Baker, A. Onions, R. J. Popplestone, T. N. Smith, *J. Chem. Soc., Perkin Trans. II* 1975, 1133-1138), rhodium, nickel (R. Baker, D. E. Halliday, T. N. Smith, *J. Organomet. Chem.* 1972, 35, C61-C63; R. Baker, *Chem. Rev.* 1973, 73, 487-530; R. Baker, A. H. Cook, T. N. Smith, *J. Chem. Soc., Perkin Trans. II* 1974, 1517-1524) and platinum have also been used as catalysts. However, the latter systems are inferior to palladium complexes in terms of activity and selectivity.

WO 91/09822 describes a continuous process using palladium acetylacetonate/2 equivalents of triphenylphosphine as catalyst. Catalyst productivities (turnover numbers) of up to 44,000 are achieved here. However, the chemoselectivities to the target product at such catalyst turnover numbers are <85%. The use of palladium complexes or palladium salts in combination with carboxylic acids for the telomerization of butadiene is known from EP 0 440 995. However, the complexing agent is not specified.

A process for the preparation of octadienyl ethers was described in 1987 by National Distillers and Chem. Corp. (U.S. Pat. Nos. 4,642,392, 4,831,183). The product mixture was separated from the catalyst (palladium acetate/5 equivalents of triphenylphosphine) by distillation, leaving the catalyst as a solution in a high-boiling solvent. The catalyst can be reused up to twelve times when supplementary phosphine is added each time. However, the initial batch (Example 1) gave the linear ether in a yield of only 57% (corresponding to a TON of 2000). The n/iso ratio of the telomers is in this case only 3.7:1. In U.S. Pat. No. 4,831, 183, the mixture was separated from the reaction solution by, for example, extraction with hexane. The telomerization was carried out in dimethylformamide or sulfolane using the catalyst mixture palladium(II) acetate/3 equivalents of triphenylphosphinemonosulfonate. Longer-chain primary alcohols such as ethanol, propanol and butanol (J. Beger, H. Reichel, *J. Prakt. Chem.* 1973, 315, 1067) also form the corresponding telomers with butadiene. However, the catalytic activity of the known catalysts is even lower here than in the abovementioned cases. Thus, under identical reaction conditions [Pd(acetylacetonate)$_2$/PPh$_3$/butadiene/alcohol =1:2:2000:5000; 60° C./10 h], the telomers of methanol are formed in a yield of 88%, those of propanol are formed in a yield of 65% and those of nonanol are formed in a yield of only 28%.

Like alcohols, carboxylic acids are suitable nucleophiles in telomerization reactions. Acetic acid and butadiene give the corresponding octadienyl derivatives in good yields (DE 2 137 291). The ratio of linear and branched products (n/iso ratio) can be influenced via the ligands on the palladium (D. Rose, H. Lepper, *J. Organomet. Chem.* 1973, 49, 473). A ratio of 4/1 was achieved using triphenylphosphine as ligand, and the ratio could be increased to 17/1 when using tris(o-methylphenyl) phosphite. Other carboxylic acids such as pivalic acid, benzoic acid and methacrylic acid, and also dicarboxylic acids, can likewise be reacted with butadiene.

Shell Oil has described a process for preparing α-olefins based on the telomerization of conjugated dienes with carboxylic acids in U.S. Pat. No. 5,030,792.

Telomerization reactions in which water is used as nucleophiles have been intensively studied by, inter alia, the Kuraray company (U.S. Pat. Nos. 4,334,117, 4,356,333, 5,057,631). In these reactions, phosphines, usually water-soluble phosphines, or phosphonium salts (EP 0 296 550) are used as ligands. The use of water-soluble disphosphines as ligands is described in WO 98/08794. DE 195 23 335 discloses the reaction of alkadienes with water in the presence of phosphonite or phosphinite ligands.

GB 1 535 718 describes the telomerization of butadiene with amines, catalyzed by palladium(0) complexes. EP 939074 and EP 773211 describes the preparation of octa-2,7-diethyl-1-amine by telomerization of ammonia and butadiene.

The telomerization of butadiene with nucleophiles such as formaldehyde, aldehydes, ketones, carbon dioxide, sulfur dioxide, sulfinic acids, β-keto esters, β-diketones, malonic esters, α-formyl ketones and silanes is likewise described in the literature.

In summary, it can be said that the known palladium-phosphine catalysts do not give satisfactory catalytic turnover numbers (TONs, catalyst productivities) in telomerization reactions of butadienes with alcohols. Industrially desired productivities of >100,000 have rarely been described for known systems. At the same time, high chemoselectivities and regioselectivities of >95% should be achieved in order to obtain an ecologically advantageous process.

SUMMARY OF THE INVENTION

It has been found that 1-olefins can be prepared in good yields and selectivities by carrying out a catalytic telomerization in the presence of a nucleophile and a palladium-carbene complex with subsequent hydrogenation of the telomer and cleavage of the hydrogenated telomer.

The present invention accordingly provides a process for preparing 1-olefins having from 8 to 16 carbon atoms by telomerization of a starting olefin having at least two conjugated bonds with a nucleophile in the presence of a palladium catalyst, hydrogenation of the telomer obtained in this way and subsequent cleavage to the 1-olefin, wherein the palladium catalyst used is a palladium-carbene complex.

DETAILED DESCRIPTION OF THE PREFERRED EMBODIMENTS

Preferred palladium complexes are ones in which the carbene carbon is bound to two nitrogen atoms. This means that the carbene ligands comprise the structural element

where C is the carbene carbon which is bound to the palladium atom.

Particularly preferred palladium-carbene complexes are ones having at least one carbene ligand of the formula I or II

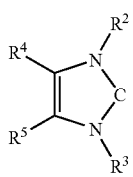

I

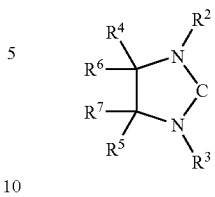

II where $R^2$ and $R^3$ are each, independently of one another, a linear, branched or cyclic $C_1$-$C_{24}$-alkyl group or a $C_5$-$C_{18}$-aryl group, where the alkyl group and the aryl group may bear, independently of one another, the substituents —CN, —COOH, —COO-alkyl-($C_1$-$C_8$), —CO-alkyl-($C_1$-$C_8$), -aryl-($C_6$-$C_{18}$), -alkyl-($C_1$-$C_{24}$), —COO-aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1$-$C_8$), —CHO, —SO$_3$H, —NH$_2$, —F, —Cl, —OH, —CF$_3$, —NO$_2$, ferrocenyl, and $R^4$ to $R^7$ are each, independently of one another, hydrogen, —CN, —COOH, —COO-alkyl-($C_1$-$C_8$), —CO-alkyl-($C_1$-$C_8$), —COO-aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1$-$C_8$), —CHO, —SO$_3$H, —NH$_2$, —F, —Cl, —OH, —CF$_3$, —NO$_2$ or a linear, branched or cyclic $C_1$-$C_{24}$-alkyl group or a $C_6$-$C_{18}$-aryl group and the alkyl group and aryl group may bear, independently of one another, the substituents —CN, —COOH, —COO-alkyl-($C_1$-$C_8$), —CO-alkyl-($C_1$-$C_8$), -aryl-($C_6$-$C_{10}$), -alkyl-($C_1$-$C_{24}$), —COO-aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1$-$C_8$), —CHO, —SO$_3$H, —NH$_2$, —F, —Cl, —OH, —CF$_3$, —NO$_2$, and the radicals $R^4$ and $R^5$ may also be part of a bridging aliphatic or aromatic ring.

The nucleophiles used in the process of the invention are preferably compounds of the formulae III, IV and V

  (III),

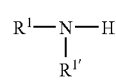  (IV)

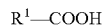  (V)

where $R^1$, $R^{1'}$ are selected independently from among hydrogen, linear, branched or cyclic $C_1$-$C_{22}$-alkyl groups, alkenyl groups, alkynyl groups, carboxyl groups and $C_5$-$C_{18}$-aryl groups, where these groups may bear substituents selected from the group consisting of —CN, —COOH, —COO-alkyl-($C_1$-$C_8$), —CO-alkyl-($C_1$-$C_8$), -aryl-($C_5$-$C_{10}$), —COO—aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1$-$C_8$), —CHO, —SO$_3$H, —NH$_2$, —F, —Cl, —OH, —CF$_3$, —NO$_2$, and the radicals $R^1$, $R^{1'}$ may be linked to one another via covalent bonds.

The process of the invention is suitable for preparing 1-olefins having 8-16 carbon atoms; the particularly preferred product is 1-octene. As starting olefins, preference is given to using 1,3-butadiene or isoprene.

In the telomerization process of the present invention, it is possible to use either pure starting olefins or mixtures of these olefins with other hydrocarbons. The further hydrocarbons are, for example, monounsaturated compounds or alkynes or cumulenes or alkanes. As 1,3-butadiene-containing mixtures, preference is given to using mixtures of 1,3-butadiene with other $C_4$- or $C_5$-hydrocarbons. Such mixtures are obtained, for example, in cracking processes for the production of ethene, in which refinery gases, naphtha, gas oil, LPG (liquefied petroleum gas), NGL (natural gas liquid), etc., are reacted. The $C_4$ fractions obtained as by-product in these processes comprise, depending on the cracking process, varying amounts of 1,3-butadiene. Typical 1,3-butadiene concentrations in the $C_4$ fraction obtained from a naphtha steam cracker are 20-70% of 1,3-butadiene.

The $C_4$ components n-butane, i-butane, 1-butene, cis-2-butene, trans-2-butene and i-butene which are likewise present in these fractions do not interfere or do not interfere significantly in the reaction in the telomerization step. On the other hand, dienes having cumulated double bonds (1,2-butadiene, allene, etc.) and alkines, in particular vinylacetylene, can act as moderators in the telomerization reaction. It is therefore advantageous to remove the $C_4$-alkynes and, if appropriate, the 1,2-butadiene beforehand (DE 195 23 335). This can, if possible, be carried out using physical methods such as distillation or extraction. Using chemical means, the alkynes can be removed by selective hydrogenation to alkenes or alkanes and the cumulated dienes can be hydrogenated to monoenes. Processes for such hydrogenations are prior art and are described, for example, in WO 98/12160, EP-A-0 273 900, DE-A-37 44 086 or U.S. Pat. No. 4,704,492.

As nucleophiles (telogens), it is possible to use all compounds which have one of the formulae III to V.

Specifically, these are:
water, ammonia
monoalcohols and phenols such as methanol, ethanol, n-propanol, isopropanol, allyl alcohol, n-butanol, i-butanol, octanol, 2-ethylhexanol, isononanol, benzyl alcohol, cyclohexanol, cyclopentanol or 2,7-octadien-1-ol, phenol
dialcohols such as ethylene glycol, 1,2-propanediol, 1,3-propanediol, 1,4-butanediol, 1,2-butanediol, 2,3-butanediol and 1,3-butanediol
hydroxy compounds such as α-hydroxyacetic esters
primary amines such as methylamine, ethylamine, propylamine, butylamine, octylamine, 2,7-octadienylamine, dodecylamine, ethylenediamine or hexamethylenediamine
secondary amines such as dimethylamine, diethylamine, N-methylaniline, bis(2,7-octadienyl)amine, dicyclohexylamine, methylcyclohexylamine, pyrrolidine, piperidine, morpholine, piperazine or hexamethyleneimine
carboxylic acids such as formic acid, acetic acid, propanoic acid, butenoic acid, isobutenoic acid, benzoic acid, 1,2-benzenedicarboxylic acid (phthalic acid).

Particularly preferred nucleophiles are methanol, ethanol, 2-ethylhexanol, octanol, octenol, octadienol, isopropanol, n-propanol, isobutanol, n-butanol, isononanol, formic acid, acetic acid, propionic acid, n-butanoic acid, isobutanoic acid, benzoic acid, phthalic acid and/or water.

Nucleophiles which can themselves be obtained via a telomerization reaction can be used directly or else can be formed in situ. Thus, for example, 2,7-octadien-1-ol can be formed in situ from water and butadiene in the presence of the telomerization catalyst, 2,7-octadienylamine can be obtained from ammonia and 1,3-butadiene, etc.

For the ratio of nucleophile to starting olefin having at least two conjugated double bonds in the telomerization reaction, the number of active hydrogen atoms in the telogen has to be taken into account. Thus, for example, methanol has one active hydrogen atom, ethylene glycol has two, methylamine has two, etc.

Preference is given to using from 0.001 mol to 10 mol of starting olefin per mole of active hydrogen atom of the nucleophile which can react with the starting olefin in the telomerization reaction. When the reaction is carried out in the liquid phase, a ratio of from 0.1 mol to 2 mol of starting olefin per mole of active hydrogen is particularly preferred.

As solvent for the telomerization reaction, use is generally made of the nucleophile employed if it is liquid under the reaction conditions. However, it is also possible to use other solvents. The solvents used should be largely inert. Preference is given to using solvents when nucleophiles which are solid under the reaction conditions are employed or in the case of products which would be formed as solids under the reaction conditions. Suitable solvents include aliphatic, cycloaliphatic and aromatic hydrocarbons, for example $C_3$-$C_{20}$-alkanes, mixtures of lower alkanes ($C_3$-$C_{20}$), cyclohexane, cyclooctane, ethylcyclohexane, alkenes and polyenes, vinylcyclohexene, 1,3,7-octatriene, the $C_4$-hydrocarbons from $C_4$ cracker fractions, benzene, toluene and xylene; polar solvents such as tertiary and secondary alcohols, amides such as acetamide, dimethylacetamide and dimethylformamide, nitriles such as acetonitrile and benzonitrile, ketones such as acetone, methyl isobutyl ketone and diethyl ketone; carboxylic esters such as ethyl acetate, ethers such as dipropyl ether, diethyl ether, dimethyl ether, methyl octyl ether, 3-methoxyoctane, dioxane, tetrahydrofuran, anisole, alkyl and aryl ethers of ethylene glycol, diethylene glycol and polyethylene glycol and other polar solvents such as sulfolane, dimethyl sulfoxide, ethylene carbonate, propylene carbonate and water. Ionic liquids, for example imidazolium or pyridinium salts, can also be used as solvents.

The solvents are used either alone or as mixtures of various solvents.

The temperature at which the telomerization reaction is carried out is in the range from 10 to 180° C., preferably from 30 to 120° C., particularly preferably from 40 to 100° C. The reaction pressure is from 1 to 300 bar, preferably from 1 to 120 bar, particularly preferably from 1 to 64 bar and very particularly preferably from 1 to 20 bar.

An essential aspect of the process of the invention is that the telomerization reaction is carried out using catalysts based on palladium complexes containing carbene ligands.

The palladium-carbene complexes can be introduced as such into the telomerization reaction or can be generated in situ during this reaction.

Examples of carbene ligands corresponding to the formulae I or II and complexes in which such ligands are present have already been described in the technical literature (W. A. Herrmann, C. Köcher, *Angew. Chem.* 1997, 109, 2257; Angew. Chem. Int. Ed. Engl. 1997, 36, 2162; V.P.W. Böhm, C.W.K. Gstöttmayr, T. Weskamp, W. A. Herrmann, *J. Organomet. Chem.* 2000, 595, 186; DE 44 47 066).

For the purposes of the present invention, carbene ligands include both free carbenes which can act as ligands and carbenes coordinated to palladium.

It is possible to use different carbene ligands at the same time in the process of the invention.

The catalyst metal palladium which forms the active catalysts under the reaction conditions can be introduced into the process in various ways.
a) As palladium-carbene complex, in which the palladium is preferably present in the oxidation state (II) or (0).
b) In the form of precursors from which the catalysts are formed in situ.

In the case of a)

Examples are palladium(0)-carbene-olefin complexes, palladium-carbene-phosphine complexes, palladium(0)-dicarbene complexes and palladium(II)-dicarbene complexes, palladium(0)-carbene-1,6-diene complexes. Compounds which can function as 1,6-diene are, for example, diallylamine, 1,1'-divinyltetramethyldisiloxane, 2,7-octadienyl ethers or 2,7-octadienylamines. Specific examples of suitable palladium-carbene complexes are shown in the following table.

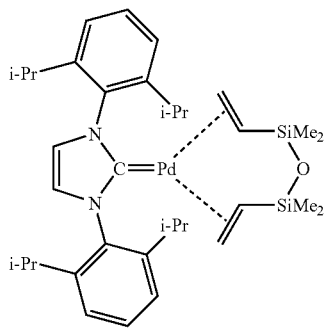

I-a

I-b

I-c

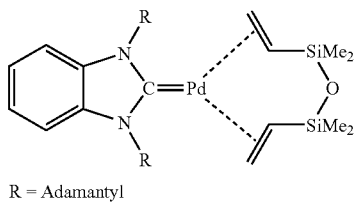

R = Adamantyl

I-d

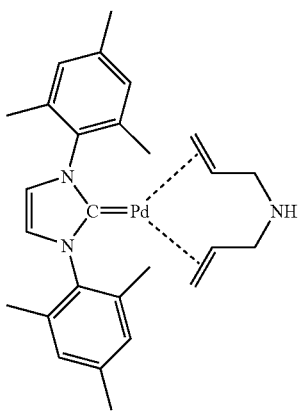

I-e

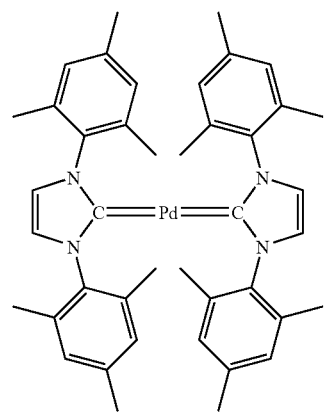

I-f

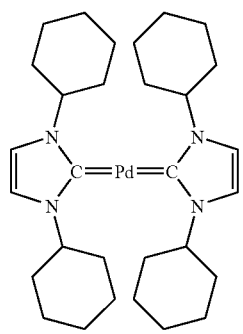

I-g

-continued

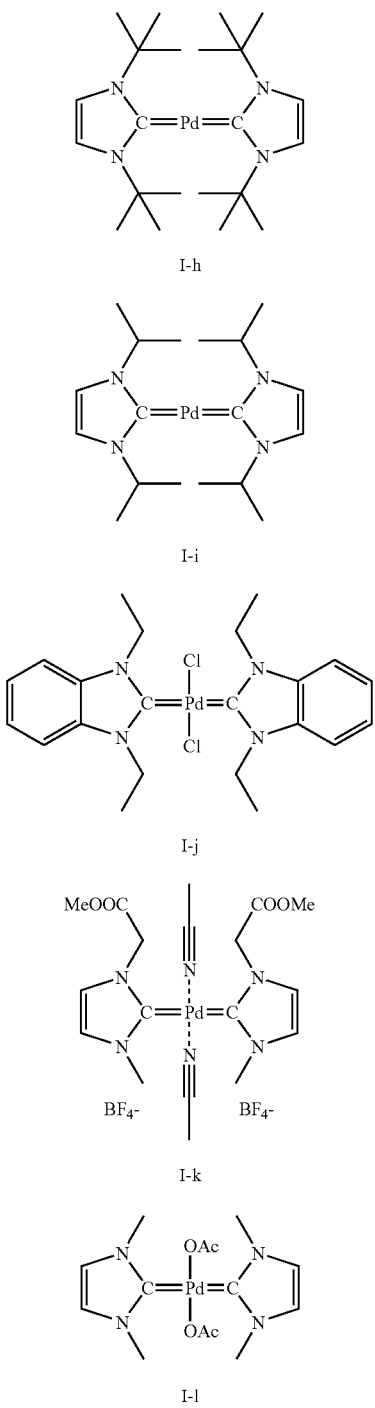

I-h

I-i

I-j

I-k

I-l

The carbene complexes of palladium to be used in the process of the invention can be prepared in a variety of ways. One simple way is, for example, the addition of carbene ligands on to palladium complexes or the replacement of ligands on palladium complexes by carbene ligands. For example, the complexes I-f to I-i are obtainable by replacement of the phosphorus ligands of the complex bis(tri-o-tolylphosphine)palladium(0) (T. Weskamp, W. A. Herrmann, *J. Organomet. Chem.* 2000, 595, 186).

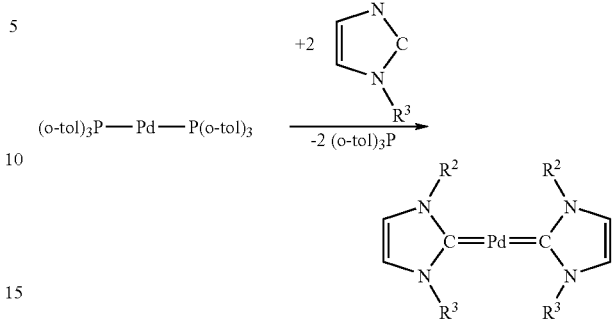

I-f $R^2=R^3$=mesityl
I-g $R^2=R^3$=c-hexyl
I-h $R^2=R^3$=t-butyl
I-i $R^2=R^3$=i-propyl In the case of b)

As precursors of the palladium catalysts, it is possible to use palladium salts such as palladium(II) acetate, palladium (II) chloride, palladium(II) bromide, lithium tetrachloropalladate, palladium(II) acetylacetonate, palladium(0)-dibenzylideneacetone complexes, palladium(II) propionate, bisacetonitrilepalladium(II) chloride, bistriphenylphosphinepalladium(II) dichloride, bisbenzonitrilepalladium(II) chloride, bis(tri-o-tolylphosphine)palladium(0) and further palladium(0) and palladium(II) complexes.

The carbenes are used in the form of free carbenes or as metal complexes or are generated in situ from carbene precursors.

Suitable precursors of the carbenes of the formulae I and II are, for example salts of the carbenes having the formulae VI and VII,

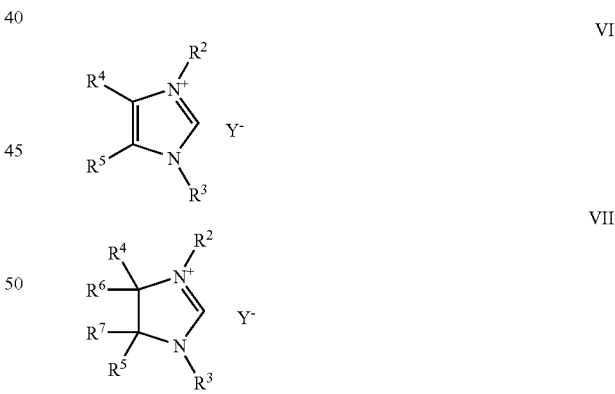

VI

VII where $R^2$, $R^3$, $R^4$, $R^5$, $R^6$, $R^7$ are as defined in formulae I and II and Y is a singly charged anionic group or, in accordance with the stoichiometry, a fraction of a multiply charged anionic group.

Examples of Y are halides, hydrogensulfate, sulfate, alkyl sulfates, aryl sulfates, borates, hydrogencarbonate, carbonate, alkyl carboxylates, phosphates or aryl carboxylates.

The corresponding carbenes can be liberated from the carbene salts by, for example, reaction with a base.

The concentration of the catalyst, formally indicated in ppm (by mass) of palladium metal based on the total mass, is from 0.01 ppm to 1000 ppm, preferably from 0.5 to 100 ppm, particularly preferably from 1 to 50 ppm.

The ratio [mol/mol] of carbene to Pd is from 0.01:1 to 250:1, preferably from 1:1 to 100:1, particularly preferably from 1:1 to 50:1.

It is possible to carry out the telomerization process in the presence of further ligands. In principle, all ligands which increase the reaction rate, improve the selectivity of the formation of the telomer, increase the catalyst life, etc., are suitable for this purpose. Examples of suitable further ligands are compounds containing one or more trivalent phosphorus, arsenic, antimony or nitrogen atoms.

Examples of phosphorus ligands are:

Phosphines such as triphenylphosphine, tris(p-tolyl)phosphine, tris(m-tolyl)phosphine, tris(o-tolyl)phosphine, tris(p-methoxyphenyl)phosphine, tris(p-dimethylaminophenyl)phosphine, tricyclohexyl-phosphine, tricyclopentylphosphine, triethylphosphine, tris(1-naphthyl)phosphine, tribenzylphosphine, tri-n-butylphosphine, tri-tert-butylphosphine, tris(3-sulfonatophenyl)phosphine (metal salt), bis(3-sulfonatophenyl)phenylphosphine (metal salt), (3-sulfonatophenyl)diphenylphosphine (metal salt), phosphites such as trimethylphosphite, triethyl-phosphite, tri-n-propylphosphite, tri-i-propyl-phosphite, tri-n-butylphosphite, tri-i-butylphosphite, tri-tert-butylphosphite, tris(2-ethylhexyl)phosphite, triphenylphosphite, tris(2,4-di-tert-butylphenyl)-phosphite, tris(2-tert-butyl-4-methoxyphenyl)phosphite, tris(2-tert-butyl-4-methylphenyl)phosphite, tris(p-cresyl)phosphite, phosphonites such as methyldiethoxyphosphine, phenyldimethoxyphosphine, phenyldiphenoxyphosphine, 2-phenoxy-2H-dibenz[c,e][1,2]oxaphosphorin and derivatives thereof in which all or some of the hydrogen atoms are replaced by alkyl and/or aryl radicals or halogen atoms, phosphinites such as diphenyl(phenoxy)phosphine and derivatives thereof in which all or some of the hydrogen atoms are replaced by alkyl and/or aryl radicals or halogen atoms, diphenyl(methoxy)phosphine, diphenyl(ethoxy)phosphine, etc.

For the purposes of the present invention, phosphonium salts can also function as further ligands. Examples of suitable phosphonium salts and their use in telomerization may be found, inter alia, in EP-A-0 296 550.

The ratio of further ligands to palladium can be from 0.1/1 to 500/1, preferably from 0.5/1 to 50/1, particularly preferably from 1/1 to 20/1 [mol/mol]. The further ligand can be introduced into the reaction as such, as a solution or in the form of metal complexes.

Additional ligand can be introduced into the reaction at any point in time and at any point in the reactor, either as such, as a solution or in the form of a metal complex.

Owing to the catalyst activities and stabilities, it is possible to use small amounts of catalyst in the process of the invention. This offers, as an alternative to a procedure in which the catalyst is reused, the option of not recycling the catalyst. Both variants have been described in the patent literature (WO 90/13531, U.S. Pat. Nos. 5,254,782, 4,642,392).

It is often advantageous to carry out the telomerization reaction in the presence of bases. Preference is given to using basic components having a $pK_b$ of less than 7, in particular compounds selected from the group consisting of amines, alkali metal salts and alkaline earth metal salts.

Suitable basic components are, for example, amines such as trialkylamines, which may be alicyclic or/and open-chain, amides, alkali metal or/and alkaline earth metal salts of aliphatic or/and aromatic carboxylic acids, e.g. acetates, propionates, benzoates, or corresponding carbonates, hydrogencarbonates, carbon dioxide, alkoxides of alkali metals and/or alkaline earth metals, phosphates, hydrogenphosphates or/and hydroxides, preferably of lithium, sodium, potassium, calcium, magnesium, cesium, or ammonium or phosphonium compounds. Preference is given to hydroxides of the alkali metals and alkaline earth metals and metal salts of the nucleophiles of the formulae III-V.

In general, the basic component is used in an amount of from 0.00001 mol % to 10 mol % (based on the starting olefin), preferably from 0.0001 mol % to 5 mol % and very particularly preferably from 0.001 mol % to 1 mol %.

Additional base can be introduced into the reaction at any point in time and at any point in the reactor, either as such or in the solution.

In the process of the invention, the ratio [mol/mol] of starting olefin used and nucleophile is from 1:100 to 100:1, preferably from 1:50 to 10:1, particularly preferably from 1:10 to 2:1.

The telomerization reaction of the process of the invention can be carried out continuously or batchwise and is not limited to the use of particular types of reactor. Examples of reactors in which the reaction can be carried out are stirred tank reactors, cascades of stirred tanks, flow tubes and loop reactors. Combinations of various reactors are also possible, for example a stirred tank reactor with a downstream flow tube.

In the process of the present invention, carbene ligands are used in telomerization reactions. Surprisingly, these catalysts are superior to the known palladium-phosphine catalysts, both in terms of selectivity and productivity. In the process of the invention, turnover numbers for the catalysts (catalyst productivities) of the order of 100,000 and more can readily be achieved, for example, in the telomerization of butadiene with alcohols.

It is also possible to carry out the telomerization in multiphase systems (for example heterogeneously catalyzed or in the presence of two liquid phases of which one comprises the catalyst). The concentration ranges in which the catalyst is used can vary. In a telomerization in a plurality of liquid phases, it is particularly advantageous for catalyst and product to be present in different phases so that the catalyst can then be separated off in a simple fashion by means of a phase separation. In such a case, water often forms one of the liquid phases. However, use is also made, for example, of perfluorinated hydrocarbons, ionic liquids and supercritical carbon dioxide (on the subject of ionic liquids, cf. P. Wasserscheid, W. Keim, Angew. Chem., Int. Ed. 2000, 39, 3772-3789). The telomerization of butadiene with water in ionic liquids is described by J.E.L. Dullius, P.A.Z. Suarez, S. Einloft, R. F. de Souza, J. Dupont, J. Fischer, A. D. Cian, Organometallics 1999, 17, 997-1000. A review of water as carrier phase for the catalyst may be found, for example, in B. Cornils, W. A. Herrmann (Eds.) "Aqueous-Phase Organometallic Catalysis", Wiley-VCH, Weinheim, New York, Chichester, Brisbane, Singapore, Toronto, 1998, pages 442-446. In the case of processes in which a plurality of liquid phases are present, it is particularly advantageous to use a telogen which is present together with the catalyst in one phase and the products are mainly present in a second phase.

When carrying out the telomerization step, the addition of other auxiliaries may bring advantages, for example the use of inhibitors which suppress the polymerization of butadiene. Such inhibitors are normally also present in commercial (stabilized) pure 1,3-butadiene. An example of a standard stabilizer is tert-butylcatechol.

The telomerization reaction is preferably not carried out to complete conversion of the starting olefin. It is frequently advantageous to limit the conversion to a maximum of 95%, preferably 88%.

The telomerization catalyst can be recovered after the telomerization reaction and all or part of it can be used for further telomerization reactions (cf. EP-A-0 218 100). The catalyst can, for example, be separated off by means of distillation, extraction, precipitation or adsorption. If all or some of the catalyst is present in a second phase, the separation can be carried out simply by separating the phases.

It is also possible for the catalyst to be modified prior to or during the separation step. This applies analogously to the complete or partial recirculation to the process which can likewise be preceded by modification of the catalyst. For example, U.S. Pat. No. 4,146,738 describes a process in which the catalyst is stabilized by means of auxiliaries prior to being separated off. After the separation from the other products, it is activated and returned to the process.

As an alternative, the catalyst can also be worked up in other ways after the reaction (cf. WO 90/13531, U.S. Pat. No. 5,254,782).

If the telogen used is not reacted completely, the excess telogen is preferably separated off from the output from the telomerization reaction and is wholly or partly returned to the reaction.

If the process of the invention is employed for preparing 1-octene by telomerization of 1,3-butadiene, by-products obtained are mainly 3-substituted 1,7-octadiene, 1,3,7-octatriene, 4-vinylcyclohexene and further $C_8$-olefins. In addition, there are small amounts of high-boiling components. For the further process, it can be advantageous to remove all or some of the by-products from the product of the telomerization reaction. In principle, it is possible to employ all methods or combinations of methods by means of which the telomer can be separated off from the product mixture. A preferred separation technique is distillation. For the separation by distillation, it is possible to use all available techniques, for example tray columns, packed columns, dividing wall columns, extracted distillation, thin film evaporators and falling film evaporators. The separation by distillation can be carried out in one or more steps and is dependent on the boiling points of the components present in the product mixture. If butadiene-containing mixtures of $C_4$-hydrocarbons are used as starting materials, the remaining $C_4$-hydrocarbons have the lowest boiling point and can therefore be separated off simply via the top.

If isobutene is present in the remaining $C_4$-hydrocarbons and alcohols are used as telogen, an additional possibility is to separate off excess alcohol together with the $C_4$-hydrocarbons and to react it further in other processes. For example, if isobutene is present in the $C_4$-hydrocarbons and methanol is used as telogen, $C_4$-hydrocarbons remaining after the telomerization can be separated off together with excess methanol and together fed to an MTBE synthesis. In addition, it may be advantageous to subject residual unreacted diene to a selective hydrogenation to the olefin prior to the separation.

Furthermore, it may be advantageous to isolate other components of the output from the telomerization reaction and, if appropriate, return them to the process or utilize them separately. This can be achieved using the techniques which have been mentioned for the abovementioned isolation. Components which may be isolated may be, for example, the telogen used, excess 1,3-butadiene, the 3-substituted 1,7-octadiene, 1,3,7-octatriene, 4-vinylcyclohexene, the base or bases used and any solvent used.

The output from the telomerization reaction is subsequently, if appropriate together with the by-products, hydrogenated by means of hydrogen or hydrogen-containing gases.

In this hydrogenation, the unsaturated olefinic double bonds are converted into single bonds.

When using alcohols as nucleophile (telogen) and 1,3-butadiene as taxogen, for example, the main products formed in the telomerization are 2,7-octadienyl ethers which are converted in the hydrogenation into n-octyl ethers. Analogously, n-octyl esters are obtained from 2,7-octadienyl esters and n-octylamines are obtained from 2,7-octadienylamine.

The hydrogenation can be carried out as a liquid-phase and/or gas-phase hydrogenation or as a combination of these techniques and can be carried out in one or more steps, for example as a prehydrogenation and a final hydrogenation.

As reactors for the hydrogenation, it is possible to use the known standard reactors for hydrogenations, for example tricklebed reactors. The heat of reaction evolved during the reaction is removed by known methods, for example by means of internal or external coolers. Specifically, this can mean the use of shell-and-tube reactors, cooling fingers, cooling coils or plates or cooling of a recycle stream (reactors with recirculation, circulation reactors).

The hydrogenation is carried out in the presence of a catalyst. It is possible to use either homogeneous or heterogeneous catalysts. Preference is given to heterogeneous catalysts which comprise at least one metal of groups 6-11 of the Periodic Table of the Elements.

The catalysts for this hydrogenation particularly preferably comprise copper, chromium and at least one metal of groups 8-10 of the Periodic Table.

When using homogeneous catalysts, ligands are used in addition to the catalyst metal. Suitable ligands are, for example, compounds of trivalent phosphorus (for example phosphines or phosphites), compounds of trivalent arsenic or antimony, nitrogen compounds (for example amines, pyridines, nitrites), halides, carbon monoxide, cyanide and carbenes.

In the case of heterogeneous catalysts, the abovementioned metals may be modified by means of other metals or moderators. Thus, for example, the activity and selectivity of heterogeneous palladium catalysts are often modified by addition of sulfur or carbon monoxide. In the case of copper catalysts, a proportion of chromium is frequently added.

The use of supported catalysts is generally advantageous since smaller amounts of metal are required and the properties of the catalyst can be additionally influenced by means of the nature of the support. Support materials which have been found to be useful are, for example, activated carbon, aluminum oxides, silicon dioxides, silicon-aluminum oxides, barium carbonate, barium sulfate or kieselguhr.

In a preferred embodiment of the present invention, a heterogeneous palladium-, nickel- or platinum-containing catalyst is used for the hydrogenation of the telomer and any unreacted starting olefins.

Particular preference is given to using supported, heterogeneous palladium or platinum catalysts in which the metal content is preferably 0.01-10%, preferably 0.1-1%.

The hydrogenations are carried out at temperatures of from 0 to 400° C., preferably from 20 to 200° C. The pressure is in the range from 0.01 to 300 bar, preferably from 0.1 to 125 bar, particularly preferably from 1 to 64 bar.

In the case of hydrogenations in the liquid phase, the weight hourly space velocity (WHSV), given in gram of substrate per gram of catalyst per hour, is preferably from 0.01 to 100 h$^{-1}$, particularly preferably 0.1-50 h$^{-1}$, very particularly preferably 0.5-10 h$^{-1}$. In the case of hydrogenations in the gas phase, the weight hourly space velocity (WHSV), given in gram of substrate per gram of catalyst per hour, is preferably from 0.1 to 200 h$^{-1}$, particularly preferably 0.5-100 h$^{-1}$, very particularly preferably 1-50 h$^{-1}$.

The hydrogenation in the liquid phase, regardless of whether it is homogeneously or heterogeneously catalyzed, can be carried out in the presence or absence of additional solvents. Examples of suitable solvents are aliphatic and cycloaliphatic hydrocarbons such as $C_3$-$C_{16}$-alkanes, mixtures of lower or higher alkanes ($C_3$-$C_{20}$), cyclohexane, cyclooctane and ethylcyclohexane; alcohols such as methanol, ethanol, propanol, isopropanol, n-butanol, isobutanol, 2-ethylhexanol, isononanol and isotridecanol; polyols such as ethylene glycol, propylene glycol, 1,3-propanediol and 1,4-butanediol; carboxylic esters such as ethyl acetate; ethers such as dipropyl ether, diethyl ether, dimethyl ether, methyl tert-butyl ether, methyl octyl ether, 3-methoxyoctane, dioxane, tetrahydrofuran, alkyl ethers of ethylene glycol, diethylene glycol and polyethylene glycol; sulfolane, dimethyl sulfoxide, ethylene carbonate, propylene carbonate and water. The solvents are used either alone or as mixtures of various solvents.

In the case of a liquid-phase hydrogenation, it is also possible for a plurality of liquid phases to be present. This method is particularly advantageous when catalyst and product are present in different phases, since the catalyst can then be separated off simply by means of a phase separation. In such cases, water often forms one of the liquid phases. However, use is also made of, for example, perfluorinated hydrocarbons, ionic liquids and supercritical carbon dioxide (on the subject of ionic liquids, cf. P. Wasserscheid, W. Keim, Angew. Chem., Int. Ed. 2000, 39, 3772-3789). A review of water as carrier phase for the catalyst may be found, for example, in B. Cornils, W. A. Herrmann (Eds.) "Aqueous-Phase Organometallic Catalysis", Wiley-VCH, Weinheim, New York, Chichester, Brisbane, Singapore, Toronto, 1998, pages 352-361.

In the hydrogenations, not only hydrogen and substrate but also other gases may be present. For example, nitrogen and/or argon or else alkanes which are gaseous under the hydrogenation conditions, for example methane, propane or butane, can be added or may already be present in the hydrogenation gas.

The hydrogenation in the process of the invention can be carried out continuously, semicontinuously or batchwise. Preference is given to a continuous hydrogenation. Largely complete conversion of the telomer is preferably strived for in the hydrogenation. However, it is also possible to stop the reaction at a partial conversion and to separate off the unreacted telomer from the remaining components and return it to the hydrogenation reaction or, if desired, utilize it in other ways.

The hydrogenation product (hydrogenated telomer) is converted into olefin and further cleavage products. It may be useful to purify the product by physical methods after the hydrogenation reaction. In principle, it is possible to employ all methods or combinations of methods by means of which the by-products can be separated wholly or partly from the hydrogenated telogen. A preferred separation technique is distillation. The separation by distillation can be carried out using all available techniques, for example tray columns, packed columns, dividing wall columns, extracted distillation, thin film evaporators and falling film evaporators. The separation by distillation can be carried out in one or more steps and is dependent on the boiling points of the components present in the product mixture.

In the cleavage process of the process of the invention, the hydrogenated telomer is cleaved to form the desired 1-olefin.

The cleavage can be carried out either in the liquid phase or in the gas phase; cleavage in the gas phase is preferred. The cleavage of the hydrogenated telomer can be carried out in the presence of any amount of other substances which are inert or largely inert under the cleavage conditions. For example, nitrogen or argon and also water, water vapor or alkanes such as methane, propane or butane can be added. The proportion of these inert materials is preferably from 0 to 98% by volume, particularly preferably from 0 to 50% by volume.

The cleavage reaction can be carried out thermally in the absence of a catalyst or in the presence of heterogeneous catalysts, in each case continuously, semicontinuously or batchwise.

In the cleavage process of the invention, the hydrogenated telomer is cleaved to form the desired 1-olefin. Cleavage reactions of this type have been described in the literature. Thus, the cleavage of alcohols and esters is a standard method for the preparation of olefins (cf. Houben-Weyl, *Methoden der Organischen Chemie*, Georg Thieme Verlag, Stuttgart, fourth edition, Volume 5/1b, page 45 ff and 105 ff).

JP 02172924 describes the cleavage of 1-octanol obtained from a telomerization reaction and subsequent hydrogenation to form 1-octene. Catalysts used are, inter alia, calcium phosphate modified with sodium hydroxide.

EP 0 440 995 describes the cleavage of alkyl esters obtained from a telomerization reaction and subsequent hydrogenation to form 1-octene. No catalysts are used in the cleavage reaction.

The cleavage of ethers is likewise known. A number of studies were published early in the 20th century, for example the cleavage of ethers over Japanese acid clay (W. Ipatiew, *Berichte der Deutschen Chemischen Gesellschaft*, 1904, 37, 2961; K. Kashima, *Bull. Chem. Soc. Jpn.* 1930, 25).

The cleavage of a methyl ether over alumina, aluminum phosphates, aluminum silicates and mixtures of aluminum silicates with metal phosphates and metal sulfates is disclosed in U.S. Pat. No. 2,561,483.

In WO 92/10450, preference is given to using acid catalysts, mainly aluminum oxides which may be modified.

CN 1158277 A claims catalysts selected from among modified $SiO_2$, thorium oxide, the oxides of the alkaline earth metals, the rare earth metals and the metals of group IV B for the cleavage of ethers. The patent application CN 1165053 describes the use of magnesium-silicon oxides for the cleavage of octyl methyl ether. Selectivities to 1-octene of over 95% at conversions of the octyl methyl ether of over 80% could be obtained using these catalysts.

In the process of the invention, the cleavage to form the 1-olefin is preferably carried out as a heterogeneously catalyzed gas-phase reaction. As catalysts, it is possible to use both acid and superacid catalysts, e.g. natural clays, acids on support materials, acidic metal oxides and metal sulfides, metal salts, metal oxides, zeolites, and also basic or strongly basic catalysts such as bases on support materials, basic metal oxides, metal salts, mixed oxides and zeolites (usually ion-exchanged with alkali or alkaline earth metals).

Examples of the abovementioned catalysts may be found, for example, in "*New solid acids and bases: their catalytic*

*properties*" by K. Tanabe et al., 1989, Elsevier Science Publishers, Amsterdam, pages 1-3.

Preference is given to using basic and strongly basic catalysts. Particular preference is given to using alkali metal hydroxides/oxides or alkaline earth metal hydroxides/oxides, optionally on support materials such as silica, alumina or carbonates. The proportion of metal hydroxides on the support is preferably from 0.01% by weight to 20% by weight, particularly preferably from 0.1% by weight to 10% by weight. Furthermore, the catalysts used for the cleavage may comprise alkali metal oxides, alkaline earth metal oxides, zinc oxide, aluminum oxide, yttrium oxide, lanthanum oxide, cerium oxide, thorium oxide, titanium oxide, zirconium oxide, tin oxide, alkali metal and alkaline earth metal carbonates, hydrogen carbonates and tungstates, mixed oxides of silicon and/or aluminum with alkali metals and alkaline earth metals, zinc, thorium, titanium, zirconium, tungsten, tin, molybdenum. Preference is likewise given to using hydrotalcites.

The catalysts are prepared by known methods. Customary methods are, for example, precipitation or impregnation and subsequent calcination.

The cleavage can be carried out at temperatures of from 100 to 800° C., preferably from 200 to 450° C., particularly preferably from 300 to 350° C. The pressure (absolute) under which the cleavage is carried out is typically from 0.1 to 25 bar. Preference is given to pressures of from 0.2 to 5 bar, particularly preferably from 1 to 2 bar. The weight hourly space velocity (WHSV), given in gram of substrate per gram of catalyst per hour, is preferably from 0.01 to 30 $h^{-1}$, particularly preferably 0.1-15 $h^{-1}$, very particularly preferably 0.5-10 $h^{-1}$.

The cleavage can be carried out to complete or partial conversion. Unreacted starting material can, after separating off the 1-olefin formed and, if appropriate, other cleavage products, be returned to the cleavage. It is also possible to separate off only the 1-olefin and, if appropriate, part of the cleavage products and recirculate the remaining material to the prepurification upstream of the actual cleavage.

The cleavage is preferably carried out to partial conversion. The conversion in this case is in the range from 10 to 95%, particularly preferably from 30 to 90%, very particularly preferably from 40 to 95%.

The target product, namely the 1-olefin, is separated off from the other components of the output from the cleavage by known methods such as phase separation, extraction, scrubbing, distillation or precipitation. A preferred process is distillation.

The nucleophile obtained in the cleavage (e.g. methanol) can optionally be returned to the telomerization reactor.

In the preparation of 1-octene from 1,3-butadiene by the process of the invention, small amounts of other $C_8$-olefins can be formed in addition to the 1-octene. Thus, 2-octene can be formed by isomerization of the 1-octene, 3-octene can be formed from the 2-octene, etc. Octane and octadienes can also be formed. To achieve a very high 1-octene purity (>97%), it can therefore be necessary to separate off part of these $C_8$ components. This purification can be carried out by distillation. It can be carried out either together with the removal of other products from the cleavage step or separately as a purification of a previously isolated $C_8$ fraction. The $C_8$-olefins having internal double bonds which are obtained as by-products in the process of the invention are themselves valuable starting materials for chemical processes, for example they can be used in hydroformylation reactions.

The 1-olefins obtained by the process of the invention are particularly suitable as comonomers in polymerization reactions of ethene or propene. 1-Octene is very particularly suitable for this purpose.

The present invention therefore also provides for the use of the 1-olefins prepared by the process described as comonomers in polymerization reactions.

The 1-olefins are preferably used as comonomers in rubbers, crosslinked or uncrosslinked polypropylene, polyethylene, ethylene-propylene blends or copolymers, EPDM-containing elastomers, polyamides, polycycloalkenes, polysiloxanes and/or PET polymers.

The present invention therefore further provides polyolefins obtained by copolymerization of at least one olefin with the 1-olefin obtained by the process described.

Preferred polyolefins are polypropylene or polyethylene (monomer: ethene and/or propene) comprising the 1-olefin prepared according to the invention, in particular 1-octene. The polyolefins preferably contain from 1 to 35 mol % of the 1-olefin.

The following examples illustrate the invention but do not restrict its scope which is defined by the description and the claims.

EXAMPLES 1-3

Telomerization of 1,3-butadiene with methanol.

Example 1

286 g of degassed methanol, 562 g of 1,3-butadiene, 0.74 g of sodium hydroxide, 50 g of cyclooctane (internal GC standard) and 0.54 g of 4-t-butylcatechol were placed under protective gas in a 3 liter autoclave (from Büchi) and the mixture was heated to 80° C. 0.0543 g of palladium acetylacetonate and 0.1208 g of 1,3-bis(2,4,6-trimethylphenyl) imidazolium chloride were dissolved separately in 47.4 g of degassed methanol under protective gas. The reaction was started by introduction of this solution (from a pressure burette) into the autoclave and the course of the reaction was followed by gas-chromatographic analysis of samples taken at regular intervals. After 180 minutes, 85% of the butadiene had reacted; after 420 minutes, more than 99% had reacted. The experiment was stopped by cooling the autoclave. The selectivity of the reaction to 2,7-octadienyl 1-methyl ether (1-methoxy-2,7-octadiene, 1-MODE) was >96% according to gas-chromatographic analysis of the output from the reactor.

Example 2

209 g of degassed methanol, 478 g of 1,3-butadiene, 1.36 g of sodium hydroxide, 50 g of cyclooctane (internal GC standard) and 0.52 g of 4-t-butylcatechol were placed under protective gas in a 3 liter autoclave (from Büchi) and the mixture was heated to 80° C. 0.0500 g of palladium acetylacetonate and 0.1253 g of 1,3-bis(2,4,6-trimethylphenyl)-4,5-dihydroimidazolium tetrafluoroborate were dissolved separately in 51 g of degassed methanol under protective gas. The reaction was started by introduction of this solution (from a pressure burette) into the autoclave and the course of the reaction was followed by gas-chromatographic analysis of samples taken at regular intervals. After 105 minutes, 85% of the butadiene had reacted; after 285 minutes, more than 98% had reacted. The experiment was stopped by cooling the autoclave. The selectivity of the reaction to 2,7-octadienyl 1-methyl ether was >96% according to gas-chromatographic analysis of the output from the reactor.

Example 3

207 g of degassed methanol, 521 g of 1,3-butadiene, 1.38 g of sodium hydroxide, 50 g of cyclooctane (internal GC standard) and 0.46 g of 4-t-butylcatechol were placed under protective gas in a 3 liter autoclave (from Büchi) and the mixture was heated to 80° C. 0.0494 g of palladium acetylacetonate and 0.1382 g of 1,3-bis(2,6-diisopropylphenyl) imidazolium chloride were dissolved separately in 49.1 g of degassed methanol under protective gas. The reaction was started by introduction of this solution (from a pressure burette) into the autoclave and the course of the reaction was followed by gas-chromatographic analysis of samples taken at regular intervals. After 210 minutes, 85% of the butadiene had reacted; after 420 minutes, more than 98% had reacted. The experiment was stopped by cooling the autoclave. The selectivity of the reaction to 2,7-octadienyl 1-methyl ether was 87% according to gas-chromatographic analysis of the output from the reactor, and the selectivity to 1,3,7-octatriene was 4%. The ratio of 2,7-octadien-1-yl methyl ether to 3-methoxyoctadiene was 91.6:8.4.

Example 4

In a Schlenk flask, 111.1 mg of sodium hydroxide and 1.6 mg of the palladium complex I-a were dissolved in 17.8 g of methanol under an argon atmosphere. The solution was transferred under protective gas to a 100 ml autoclave (from Parr), the autoclave was cooled and 15 g of 1,3-butadiene were condensed in. The autoclave was heated at 90° C. for 16 hours. During this time, 87% of the 1,3-butadiene reacted. The selectivity of the reaction to l-methoxyocta-2,7-diene was 95% and that to 3-methoxyocta-1,7-diene was 2.4%.

Example 5

6.4 kg of methanol were placed in a 70 l steel autoclave. 35 g of sodium hydroxide were dissolved in the methanol, and 1.9 g of 4-t-butylcatechol, 1.8 g of palladium(II) acetate and 6 g of 1,3-bis(2,4,6-trimethylphenyl) imidazolium chloride were added to this solution. After addition of 15 kg of 1,3-butadiene, the autoclave was heated. After commencement of the exothermic reaction (at about 70° C.), the internal temperature rose to a maximum of 125° C., after which the reaction mixture cooled down again and was kept constant at 80° C. by heating. After 6 hours, the reactor was cooled to room temperature. According to GC analysis, 95% of the 1,3-butadiene had reacted, and the selectivity to 1-methoxyocta-2,7-diene was 93.0% and that to 3-methoxyocta-1,7-diene was 2.9%.

EXAMPLES 6-9

Hydrogenation of the telomers

The reaction mixtures were analyzed by gas chromatography on an FFAP column from Hewlett-Packard. As hydrogenation catalyst, use was made of the commercial catalyst H 14184r, produced by Degussa AG. Its properties are described as follows by the manufacturer:

| | |
|---|---|
| Pd content | 0.5% by weight |
| Support | $Al_2O_3$ |
| Form | extrudates |
| Diameter | 1.2 mm |
| Length | 2-8 mm |
| Bulk density | 600 kg/m$^3$ |
| BET surface area | 200 m$^2$/g |
| Specific pore volume | 0.65 cm$^3$/g |
| Reduction method | none, catalyst is prereduced |

Example 6

50 g of the catalyst were placed in the catalyst basket of a 1000 ml pressure reactor and 492 g of liquid 1-methoxy-2,7-octadiene (1-MODE) were added. The trans/cis ratio in the 1-MODE was 0.94. The hydrogenation of the 1-MODE was carried out using pure hydrogen at a pressure of 20 bar and a temperature of 40° C. The hydrogenation was finished after 10 hours. The conversion of 1-MODE was then 99.9%. The yield of 1-methoxyoctane (1-MOAN) was 99.9%.

Example 7

50 g of the catalyst were placed in the catalyst basket of a 1000 ml pressure reactor and 492 g of liquid 1-methoxy-2,7-octadiene (1-MODE) were added. The trans/cis ratio in the 1-MODE was 0.94. The hydrogenation of the 1-MODE was carried out using pure hydrogen at a pressure of 20 bar and a temperature of 60° C. The hydrogenation was finished after 6 hours. The conversion of 1-MODE was then 99.9%. The yield of 1-methoxyoctane (1-MOAN) was 99.9%.

Example 8

50 g of the catalyst were placed in the catalyst basket of a 1000 ml pressure reactor and 492 g of liquid 1-methoxy-2,7-octadiene (1-MODE) were added. The trans/cis ratio in the 1-MODE was 0.94. The hydrogenation of the 1-MODE was carried out using pure hydrogen at a pressure of 30 bar and a temperature of 40° C. The hydrogenation was finished after 5.5 hours. The conversion of 1-MODE was then 99.9%. The yield of 1-methoxyoctane (1-MOAN) was 99.9%.

Example 9

50 g of the catalyst were placed in the catalyst basket of a 1000 ml pressure reactor and 492 g of liquid 1-methoxy-2,7-octadiene (1-MODE) were added. The trans/cis ratio in the 1-MODE was 0.94. The hydrogenation of the 1-MODE was carried out using pure hydrogen at a pressure of 30 bar and a temperature of 60° C. The hydrogenation was finished after 4 hours. The conversion of 1-MODE was then 99.9%. The yield of 1-methoxyoctane (1-MOAN) was 99.9%.

Example 10

Cleavage Over an Acid Catalyst

The product of the hydrogenation, viz. 1-methoxyoctane (1-MOAN, methyl n-octyl ether) was used in a purity of about 98% by weight (2% of high boilers) for the cleavage in the presence of a silica-alumina catalyst in a flow-through fixed-bed reactor. The catalyst was a commercial catalyst designated as K306 from Süd-Chemie AG.

The liquid starting material was vaporized at 220° C. in a vaporizer before entering the reactor. At a reaction temperature of 250° C. in the reactor, 7.7 g/h of starting material were passed in gaseous form through 10 g of catalyst in granule form, corresponding to a WHSV of 0.77 h$^{-1}$. The gaseous product was cooled in a condenser and collected in liquid form in a glass receiver.

The GC analysis of the cleavage product is shown in Table 1.

TABLE 1

Cleavage of 1-MOAN over the silica-alumina catalyst K306

| Component | Products of the cleavage of MOAN (% by weight) |
|---|---|
| 1-Octene | 2.7 |
| t-4-Octene | 2.0 |
| t-3-Octene/c-4-octene | 5.3 |
| c-3-Octene | 1.6 |
| t-2-Octene | 6.2 |
| c-2-Octene | 3.8 |
| Methanol | 6.2 |
| 1-MOAN | 67.1 |
| Remainder | 5.1 |

As can be seen from Table 1, 1-MOAN is cleaved to the desired product 1-octene with a relatively low selectivity to 1-octene (≈8.7%).

Example 11

The product of the hydrogenation, viz. 1-methoxyoctane (1-MOAN, methyl n-octyl ether) was used in a purity of about 98% by weight (2% of high boilers) for the cleavage in the presence of an aluminum oxide modified with sodium hydroxide (Al$_2$O$_3$ containing 1% by weight of Na$_2$O) in a flow-through fixed-bed reactor.

The liquid starting material was vaporized at 220° C. in a vaporizer before entering the reactor. At a reaction temperature of 350° C. in the reactor, 20 g/h of starting material were passed in gaseous form through 18 g of catalyst in spherical form, corresponding to a WHSV of 1.1 h$^{-1}$. The gaseous product was cooled in a condenser and collected in liquid form in a glass receiver.

The GC analysis of the cleavage product is shown in Table 2.

TABLE 2

Cleavage of 1-MOAN over the Na-modified Al$_2$O$_3$ catalyst

| Component | Products of the cleavage of 2-octanol [sic] (% by weight) |
|---|---|
| 1-Octene | 32.95 |
| t-4-Octene | 0.02 |
| t-3-Octene/c-4-octene | 0.01 |
| c-3-Octene | 0.01 |
| t-2-Octene | 0.77 |
| c-2-Octene | 1.25 |
| Methanol | 9.16 |
| MOAN | 47.38 |
| Remainder | 8.47 |

As can be seen from Table 2, 1-MOAN is cleaved to the desired product 1-octene with a high selectivity to 1-octene (>92%).

The by-products listed under "Remainder" comprise components which can likewise be cleaved to form 1-octene, including dioctyl ether. These, too, can, if desired, be recirculated to the cleavage.

The invention claimed is:

1. A process for preparing a 1-olefin having from 8 to 16 carbon atoms by telomerization, comprising:
    telomerizing a starting olefin having at least two conjugated bonds with a nucleophile in the presence of a palladium complex catalyst that contains at least one ligand which contains a carbene atom which is directly bonded to the palladium atom, hydrogenating the telomer obtained; and
    subsequently cleaving the hydrogenated telomer to the 1-olefin.

2. The process as claimed in claim 1, wherein the carbene ligand comprise the structural element

wherein C is the carbene carbon which is bonded to the palladium atom.

3. The process as claimed in claim 2 wherein the carbene ligand is one or more compounds of formula I or II

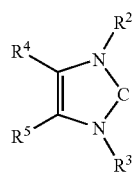

I

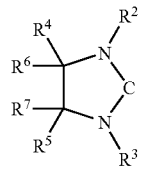

II wherein R$^2$ and R$^3$ are each, independently of one another, a linear, branched or cyclic C$_1$-C$_{24}$-alkyl group or a C$_5$-C$_{18}$-aryl group, where the alkyl group and the aryl group may bear, independently of one another, the substituents —CN, —COOH, —COO-alkyl-(C$_1$-C$_8$), —CO-alkyl -(C$_1$-C$_8$), -aryl-(C$_6$-C$_{18}$), -alkyl-(C$_1$-C$_{24}$), —COO-aryl-(C$_6$-C$_{10}$), —CO-aryl-(C$_6$-C$_{10}$), —O-alkyl -(C$_1$-C$_8$), —O—CO-alkyl-(C$_1$-C$_8$), —N-alkyl$_2$-(C$_1$-C$_8$), —CHO, —SO$_3$H, —NH$_2$, —F, —Cl, —OH, —CF$_3$, —NO$_2$, ferrocenyl, and R$^4$ to R$^7$ are each, independently of one another, hydrogen, —CN, —COOH, —COO-alkyl-(C$_1$-C$_8$), —CO-alkyl-(C$_1$-C$_8$), —COO-aryl-(C$_6$-C$_{10}$), —CO-aryl-(C$_6$-C$_{10}$), —O-alkyl -(C$_1$-C$_8$), —O—CO-alkyl-(C$_1$-C$_8$), —N-alkyl$_2$-(C$_1$-C$_8$), —CHO, —SO$_3$H, —NH$_2$, —F, —Cl, —OH, —CF$_3$, —NO$_2$ or a linear, branched or cyclic C$_1$-C$_{24}$-alkyl group or a C$_6$-C$_{18}$-aryl group and the alkyl group and aryl group may bear, independently of one another, the substituents —CN, —COOH, —COO-alkyl-(C$_1$-C$_8$), —CO-alkyl-(C$_1$-C$_8$), -aryl-(C$_6$-C$_{10}$), -alkyl-(C$_1$-C$_{24}$), —COO-aryl-(C$_6$-C$_{10}$), —CO-aryl-(C$_6$-C$_{10}$), —O-alkyl-($C_1$-$C_8$), —O—CO-alkyl-($C_1$-$C_8$), —N-alkyl$_2$-($C_1$-$C_8$), —CHO, —SO$_3$H, —NH$_2$, —F, —Cl, —OH, —CF$_3$, —NO$_2$, and the radicals $R^4$ and $R^5$ may also be part of a bridging aliphatic or aromatic ring.

4. The process as claimed in claim 1, wherein said nucleophile is a compound of formulae III, IV or V

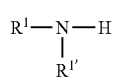

(IV)

wherein $R^1$ and $R^{1'}$ are selected independently from the group consisting of hydrogen, linear, branched or cyclic $C_1$-$C_{22}$-alkyl groups, alkenyl groups, alkynyl groups, carboxyl groups and $C_5$-$C_{18}$-aryl groups, where these groups may bear substituents selected from the group consisting of —CN, —COOH, —COO-alkyl-($C_1$-$C_8$), —CO-alkyl-($C_1$-$C_8$), -aryl-($C_5$-$C_{10}$), —COO-aryl-($C_6$-$C_{10}$), —CO-aryl-($C_6$-$C_{10}$), —O-alkyl-($C_1$-$C_8$), —O—CO-alkyl-($C_1$-$C_8$), —N-alkyl$_2$-($C_1$-$C_8$), —CHO, —SO$_3$H, —NH$_2$, —F, —Cl, —OH, —CF$_3$, —NO$_2$, and the radicals $R^1$, $R^{1'}$, may be linked to one another via covalent bonds.

5. The process as claimed in claim 1, wherein said nucleophile is methanol, ethanol, 2-ethylhexanol, octanol, octenol, octadienol, isopropanol, n-propanol, isobutanol, n-butanol, isononanol, formic acid, acetic acid, propionic acid, n-butanoic acid, isobutanoic acid, benzoic acid, phthalic acid, water, and mixtures thereof.

6. The process as claimed in claim 1, wherein the telomerization is carried out only to a conversion of the starting olefin of not more than 95%.

7. The process as claimed in claim 1, wherein the telomer is hydrogenated in the presence of a heterogeneous or homogeneous catalyst.

8. The process as claimed in claim 7, wherein said telomer is hydrogenated in the presence of a heterogeneous catalyst comprising at least one metal of groups 6-11 of the Periodic Table of the Elements.

9. The process as claimed in claim 8, wherein said hydrogenated telomer is cleaved in the presence of a basic or strongly basic or an acidic or strongly acidic catalyst.

10. The process as claimed in claim 9, wherein said hydrogenated telomer is cleaved in the presence of a catalyst comprising alkali metal hydroxides/oxides or alkaline earth metal hydroxides/oxides.

11. The process as claimed in claim 1, wherein said hydrogenated telomer is cleaved in the presence of a catalyst selected from the group consisting of alkali metal oxides, alkaline earth metal oxides, zinc oxide, aluminum oxide, yttrium oxide, lanthanum oxide, cerium oxide, thorium oxide, titanium oxide, zirconium oxide, tin oxide, alkali metal and alkaline earth metal carbonates, hydrogencarbonates or tungstates.

12. The process as claimed in claim 1, wherein said hydrogenated telomer is cleaved in the presence of a catalyst selected from the group consisting of hydrotalcites, mixed oxides of silicon and/or aluminum with alkali metals and alkaline earth metals, zinc, thorium, titanium, zirconium, tungsten, tin and molybdenum.

13. The process as claimed in claim 1, wherein the cleavage of the hydrogenated telomer is carried out in the gas phase.

14. The process as claimed in claim 13 wherein the cleavage of the hydrogenated telomer is carried out at temperatures in the range from 100 to 800° C.

15. The process as claimed in claim 1, wherein the cleavage of the hydrogenated telomer is carried out to a conversion of the hydrogenated telomer of 10-95%.

16. The process as claimed in claim 1, wherein 1,3-butadiene or isoprene is the starting olefin having at least two conjugated double bonds.

17. The process as claimed in claim 16, wherein the starting olefin is admixed with other hydrocarbons.

18. The process as claimed in claim 1, wherein the telomerization is carried out at temperatures ranging from 10 to 180° C. and a pressure of from 1 to 300 bar.

19. The process as claimed in claim 1, wherein the ratio of carbene ligand to Pd (mol/mol) ranges from 0.01:1 to 250:1.

20. The process as claimed in claim 1, wherein the palladium-carbene complex is introduced as such into the telomerization reaction.

21. The process as claimed in claim 1, wherein the palladium-carbene complex is generated in situ during the telomenzation reaction.

22. The process as claimed in claim 1, wherein the carbene ligand is generated in situ during the telomerization reaction.

23. The process as claimed in claim 1, wherein a basic component having a p$K_b$ of <7 is added to the telomerization reaction.

24. The process as claimed in claim 1, wherein the palladium concentration in the reaction mixture of the telomerization ranges from 0.01 to 1000 ppm.

* * * * *